United States Patent
Pierrat et al.

(10) Patent No.: US 6,272,236 B1
(45) Date of Patent: *Aug. 7, 2001

(54) INSPECTION TECHNIQUE OF PHOTOMASK

(75) Inventors: Christophe Pierrat, Boise, ID (US); James Burdorf, Tualatin, OR (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/618,503

(22) Filed: Jul. 18, 2000

Related U.S. Application Data

(63) Continuation of application No. 09/028,878, filed on Feb. 24, 1998, now Pat. No. 6,091,845.

(51) Int. Cl.[7] .................................................. G06K 9/82
(52) U.S. Cl. .............................. 382/144; 438/16; 716/21
(58) Field of Search .................................... 382/144, 145, 382/149, 151, 157, 266, 285; 356/384, 390, 394, 237.4, 237.5; 348/87, 126, 129, 130; 438/16; 250/559.04, 559.05, 559.06, 559.07, 559.08, 559.2, 559.39, 559.45, 559.46; 703/13, 14; 716/19, 21, 22; 702/40, 159; 430/30

(56) References Cited

U.S. PATENT DOCUMENTS

| | | | |
|---|---|---|---|
| 4,628,531 | 12/1986 | Okamoto et al. | 382/8 |
| 4,633,504 | 12/1986 | Wihl | 382/54 |
| 4,641,353 | * 2/1987 | Kobayashi | 382/8 |
| 4,669,123 | * 5/1987 | Kobayashi et al. | 382/8 |
| 4,958,374 | * 9/1990 | Tokita et al. | 382/8 |
| 5,023,328 | 6/1991 | Pierrat | 356/237.4 |
| 5,293,557 | 3/1994 | Fujinaga et al. | 364/578 |
| 5,307,421 | 4/1994 | Darboux et al. | 382/8 |
| 5,475,766 | 12/1995 | Tsuchiya et al. | 382/144 |
| 5,481,624 | 1/1996 | Kamon | 382/144 |
| 5,513,275 | 4/1996 | Khalaj et al. | 382/149 |
| 5,572,598 | 11/1996 | Wihl et al. | 382/144 |
| 5,582,939 | 12/1996 | Pierrat | 430/5 |
| 5,621,652 | 4/1997 | Eakin | 364/490 |
| 5,633,713 | * 5/1997 | Tanaka et al. | 356/355 |
| 5,736,280 | * 4/1998 | Tsudaka | 430/30 |
| 5,745,388 | * 4/1998 | Mimotogi et al. | 364/578 |
| 5,801,954 | 9/1998 | Le et al. | 364/488 |
| 5,804,340 | 9/1998 | Garza et al. | 430/5 |
| 5,849,440 | 12/1998 | Lucas et al. | 430/5 |
| 5,889,678 | 3/1999 | Inoue et al. | 364/488 |
| 5,889,686 | 3/1999 | Mimotogi et al. | 364/578 |
| 5,965,306 | * 10/1999 | Mansfield et al. | 430/22 |
| 6,014,456 | 1/2000 | Tsudaka | 382/144 |
| 6,067,375 | * 5/2000 | Tsudaka | 382/144 |
| 6,081,659 | * 6/2000 | Garza et al. | 395/500.22 |

OTHER PUBLICATIONS

Koppelman, G.M., "Oyster, a 3D Structural Simulator for Micro Electromechanical Design", *Micro Electro Mechanical Systems, IEEE 1989 Proceedings, an Investigation of Micro Structures, Sensors, Actuators, machines and Robots*, 88–93, (Feb. 1989).

Wolf, S., et al., *Silcon Processing for the VLSI ERA, vol. 1: Process Technology*, Lattice Press, Sunset Beach California, 56–59; 189–191, (1990).

* cited by examiner

Primary Examiner—Leo Boudreau
Assistant Examiner—Brian P. Werner
(74) Attorney, Agent, or Firm—Schwegman, Lundberg, Woessner & Kluth, P.A.

(57) ABSTRACT

An improved technique for inspecting photomasks employs simulated images of the resist pattern. A simulated image of an original pattern is compared to a simulated image generated from a pattern captured from a photomask manufactured from the original pattern. Alternatively, simulated images generated from captured data from two different instances of the same original pattern formed in a photomask are compared.

32 Claims, 5 Drawing Sheets

INSPECTION TECHNIQUE OF PHOTOMASK

This application is a Continuation of U.S. Ser. No. 09/028,878, filed Feb. 24, 1998, now Pat. No. 6,091,845.

FIELD OF THE INVENTION

The present invention relates in general to manufacturing semiconductor devices, and particularly to methods and apparatus for detecting defects introduced during the photolithography process.

BACKGROUND OF THE INVENTION

Defects in masks have always been a source of yield reduction in integrated circuit manufacture. As the minimum sizes approach 1 μm and below, and the circuits are designed with higher device densities, defects that were once tolerable can no longer be accepted. Common sources of defects are incorrect design of the mask patterns and flaws introduced into the patterns during the pattern generation process. Because each mask is printed on large numbers of wafers, fatal defects in a mask are highly undesirable. It would be useful if such defects could be detected and repaired prior to printing.

Device features are primarily fabricated using photolithography. The art of photolithography embodies techniques for creating two-dimensional patterns on a work surface by the controlled application of energy (such as electromagnetic, ion beam or other radiation) to a reactive material deposited on a wafer. In a photolithographic process the energy application is controlled through the use of a patterned photomask. The pattern is transferred to a photoresist coating on the wafer surface, forming a resist pattern. The wafer is then etched according to the resist pattern and, following the etch, subjected to further processing steps. The resulting features are the basis of the final circuit. As can be seen, the accuracy of the mask pattern and the resist pattern play important roles in the quality of the circuit. As area and feature size decreases, the impact of pattern defects and optical effects increases proportionately. Defects in either the mask or resist pattern during processing may have a direct affect on the accuracy and electronic characteristics of the semiconductor device.

Mask fabrication defects have a variety of causes. Such causes include, but are not limited to, defects in the original substrate, introduction of particulate matter during fabrication, scratches, or improper processing. In an attempt to minimize the number of defects introduced during wafer processing, photomasks are inspected after they are created and before they are used to pattern the wafers. Conventional inspection procedures examine several characteristics of the mask, including line width measurement, measurement of the pattern registration, whether all features present in the design database have been transferred to the mask, and whether any mask fabrication defects have been produced while manufacturing the mask. Current systems employ different inspection tools and methods for each of the above inspections. Originally, inspections were carried out by a human operator. As masks have become more complex this task has been relegated to automatic detection systems which perform the task more rapidly, with better sensitivity and repeatability and with fewer errors.

Some conventional inspection systems reduce material costs by comparing an image of the mask to the original data U.S. Pat. No. 5,481,624, issued to Kamon et al., entitled "Mask Inspecting Method and Mask Detector," describes an inspection method similar to that disclosed in U.S. Pat. No. 4,641,353, issued to Kobayashi, entitled "Inspection Method and Apparatus for a Mask Pattern Used in Semiconductor Device Fabrication." Kamon's method is directed to phase shifting masks, which include extra features in the mask to account for the unique optical effects of the phase shifting material used to manufacture the mask. Both Kobayashi and Kamon expose the actual pattern embedded in the mask using the same optical conditions as those used in a wafer exposure and compare that to the original pattern data These methods are an attempt to detect defects in the pattern before it is printed on wafers.

In a conventional die-to-database system such as that described in Kobayashi, the data defining the original pattern is compiled and prepared. A photomask is then fabricated using the original pattern data. The conventional inspection system acquires a two dimensional image from the photomask and conditions the resulting image. Conditioning the two-dimensional image cleans it up and enhances the image for future processing. The original pattern data is reformatted into a two-dimensional binary image acceptable to the inspection system. The reformatted data image is then converted to gray scale and filtered to resemble an acquired two-dimensional image. The two images are then aligned, and any discrepancies between the two images are flagged as potential defects. A conventional die-to-die inspection system works in a similar fashion. The primary difference is, instead of formatting one set of data from the original pattern data, mask data from two pattern images acquired from the mask are compared to each other.

Conventional inspection systems detect defects in any one of three images: that defined by the original data from which the mask is constructed; the pattern after it is printed on the mask; or the pattern after it has been printed on the wafer. In conventional systems, any inspection at a given stage of the process will potentially pick up anomalies introduced at that or earlier stages. However, using conventional inspection tools, many defects are not noticeable until the feature is produced in three dimensions by forming the pattern in the resist, due at least in part to the fact that defect printabilities the resist is a function of the exposure tool and of the resist characteristics. Defects which appear at this stage, however, are more costly to repair. When defects are discovered prior to resist processing, only a single mask need be repaired or replaced. Defects not discovered until after the resist is formed are likely not found until they have been replicated over large numbers of wafers. All of the affected wafers must then either be repaired or discarded. What is needed is a way to anticipate these less obvious defects before resist processing begins.

Existing inspection methods are limited because they are unable to anticipate the defects which appear when the resist is formed on the patterned wafer. Such defects result from defects in the pattern as well as from characteristic behavior of the expose tool or the resist material during processing. Existing methods do not take into account the characteristics of the expose tool or the resist material which will be formed according to the mask pattern. As a result, a mask may be inaccurately flagged as defective where, even though the mask pattern and original pattern are not identical, the "defect" would not impact the final resist pattern. Alternatively, there may be subtle mask defects that are not captured using conventional inspection techniques, but which cause resist defects due to the characteristics of the exposure tool and the resist material. The mask is, as a result, inaccurately flagged defect-free, when in fact one or more defects will appear when the resist is formed according to the pattern. What is needed is a way to accurately identify "true" defects at a point where they can be corrected or avoided at lower cost.

Systems which do not identify defects until after the pattern has been printed on the wafer increase process costs because each defect is likely repeated over a number of wafers before it is discovered. What is needed is a reliable way to determine, prior to forming the resist, whether resist formed according to a particular pattern will contain any defects. Such a system would reduce production costs.

SUMMARY OF THE INVENTION

The present invention eliminates the aforementioned drawbacks of the prior art. In contrast to conventional systems, the system of the present invention is a combination of image simulation procedures, providing extended defect detection capability to anticipate defects which would not otherwise be found until after the resist is formed. Conventional systems are limited in that they only compare mask images. A single correction in a mask pattern prior to printing and etching can prevent many defects since each mask pattern is printed on a number of wafers during the fabrication process. If the defect is not found until after resist formation, the number of integrated circuit devices which must be repaired and potentially thrown away increases dramatically. Many defects, however, do not appear until the three-dimensional feature is created during resist processing.

The present invention also provides a method of a mask inspection which uses available technology in a novel fashion to detect, before the resist is formed, defects which are likely to occur in the resist. In anticipating potential defects the system and method of the invention considers the effect of resist characteristics.

One embodiment of the present invention provides the ability to inspect defect printability instead of inspecting defects in the chrome. Because the printability of defects is amplified by resist processing, accounting for resist effects in the inspection process reduces the number of costly defects occurring during resist processing.

According to another embodiment the present invention provides an inspection system and method which can be used with both die-to-database and die-to-die inspections.

A method of inspecting a pattern on a mask is provided in another embodiment of the present invention In one implementation the mask pattern is manufactured from original pattern data, the mask comprising one or more copies of the pattern. The method comprises the steps of creating a first simulation of resist formed according to the original pattern data, capturing an inspection image of a portion of the mask, creating a second simulation of resist formed according to the inspection image, and comparing the first simulation to the second simulation.

According to another embodiment the first simulation is performed off-line. In one embodiment the pattern data is tree dimensional, while in another embodiment it is two-dimensional. In a further embodiment the inspection image comprises three-dimensional data, while in another embodiment it comprises two-dimensional data. According to another embodiment the simulations are three-dimensional. In a further embodiment the simulations are two-dimensional.

Yet another embodiment of the present invention describes a mask inspection system, wherein the mask has a plurality of identical patterns generated from a pattern. The mask inspection system also comprises an inspection device for capturing image data of a pattern in the mask, circuitry for using the captured image data to create an image of resist formed according to the pattern, circuitry for using the pattern data used to form the mask pattern to create a second image of resist formed, and circuitry for comparing the first image to the second image.

According to another embodiment of the present invention, a mask inspection system is provided, comprising a mask which comprises one or more patterns, including a first pattern and a second pattern, wherein the first pattern and the second pattern are generated from the same original pattern data. In addition, in this embodiment, the mask inspection system provides an inspection device for capturing image data of the one or more patterns, circuitry for creating an image of resist formed according to the first pattern using captured image data, circuitry for creating an image of resist formed according to the second pattern using captured image data, and circuitry for comparing the image of the first pattern to the image of the second pattern.

Yet another embodiment describes a computer program product which comprises a computer usable medium having a computer readable code means embodied therein for emulating an image. According to this embodiment the computer readable program code comprises means for causing a computer to read a first set of digitized image data, generate a first image from the first set of digitized data, read a second set of digitized image data, and generate a second image from the second set of digitized data. In a further embodiment, the computer readable program means comprises computer readable program means for incorporating resist characteristics in the generated images.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DETAILED DESCRIPTION OF THE PREFERRED EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following detailed description is, therefore, not to be taken in a limiting sense, and the scope of the present invention is defined by the appended claims.

Figure 1:
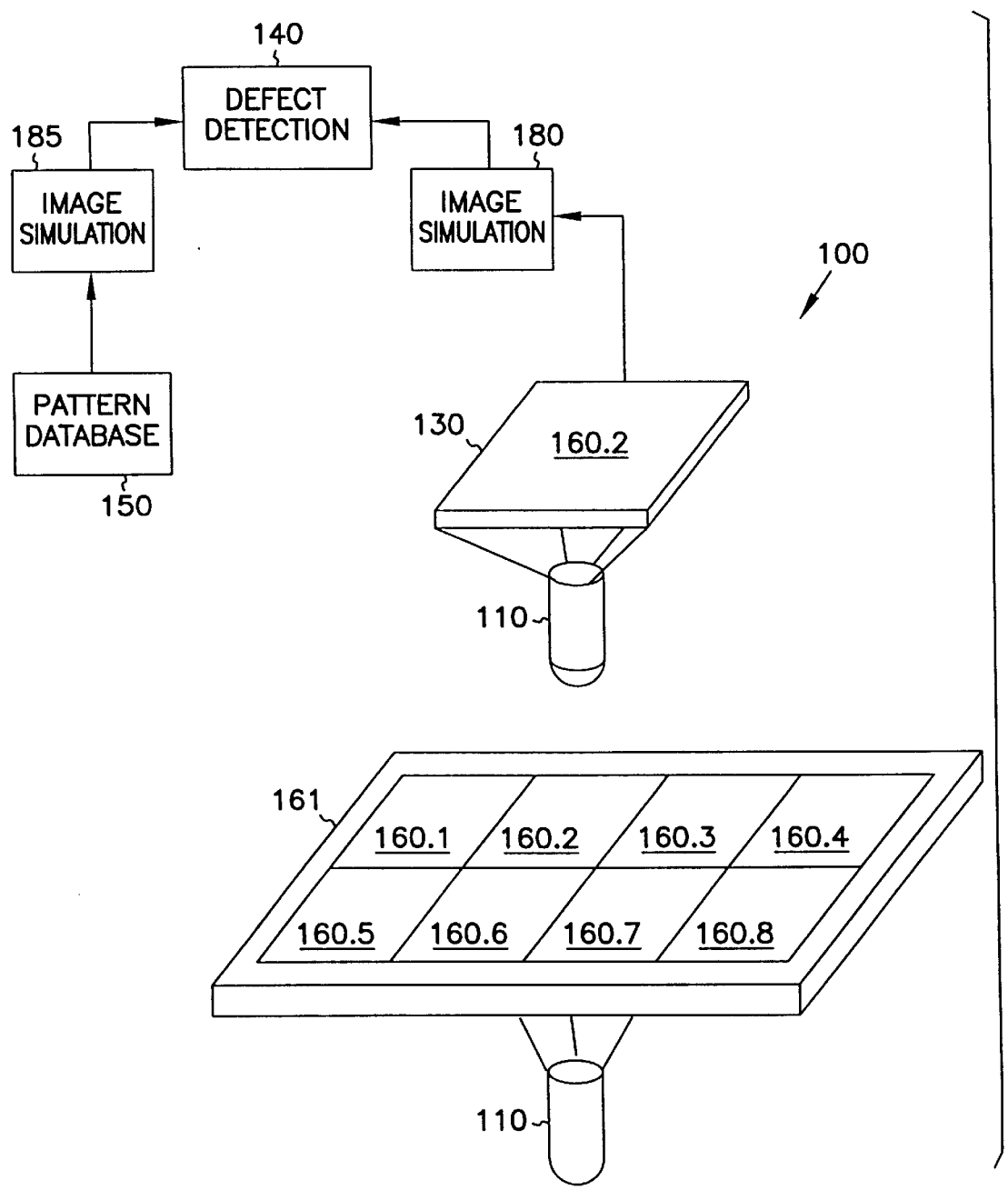
FIG. 1 illustrates a die-to-database inspection system according to one embodiment of the present invention.

The method and apparatus of the present invention improves the sensitivity of mask inspection machines 100. In one embodiment of the present invention, die-to-database inspection is provided as shown in FIG. 1. Mask 161 has a plurality of identical mask patterns 160.1–160.8, wherein mask patterns 160.1–160.8 are formed from the same pattern, as represented by pattern database 150.

First, mask pattern 160.2 is exposed to energy source 110 and projected onto image sensor 130. The mask image is then acquired using inspection machine 100. The image acquisition process is well known in the art, and is incorporated in a variety of conventional inspection machines. These include a scanning electron microscope (SEM) inspection machines such as the KLA SEMSPEC™, an aerial image measurement system such as MSM-100™ from Zeiss, Inc. or an optical inspection machine. One skilled in the art will recognnre that any image from any inspection tool can be used as input into the system of the invention.

Mask inspection machines 100 is not limited to any particular type of mask. In fact, the inspection machine is applicable to the following types of masks: a photomask, an ion projection mask, an e-beam projection mask, a x-ray projection mask, a x-ray mask, a mask with proximity effect correction, and a phase shifting mask Those skilled in the art will readily recognize that a wide variety of types of masks may be inspected using the present invention other than the ones listed here.

The image acquisition process generates simulated image 180. According to one embodiment of the invention, this image may be a three-dimensional image, while in a second embodiment the image data acquired is two-dimensional. In the context of the present discussion "three-dimensional" means that, for every point of the image, the x position, y position, and visual properties (such as intensity) are identified. In the same manner, "two dimensional" means that, for every point of the image, only the x position, y position, and binary state of the point are recorded.

Where a three-dimensional image provides a complete representation of the image, a two-dimensional image provides what is essentially an outline of the image. One skilled in the art will recognize that a three-dimensional image comprises a significantly larger amount of data than a two-dimensional image.

As shown in FIG. 1, the resulting digitized image of 160.2, whether two-or three-dimensional, is sent to image simulation circuitry, where it is used to construct image simulation 180. In a similar manner, image data derived from original pattern data 150 is processed through image simulation circuitry, creating second simulated image 185.

In one embodiment, image simulations 180 and 185 are three-dimensional. This embodiment provides a more complete and accurate rendition of the image, enhancing the benefits of the image comparison to be performed in following steps. In an alternate embodiment image simulation 180 and 185 are two-dimensional. The two-dimensional model provides a significant reduction in the amount of data that is processed by associated procedures and image simulation circuitry corresponding to image simulations 180 and 185.

In one embodiment, image simulation circuitry corresponding to image simulations 180 and 185 comprises program logic which adds elevation data to the input image. According to one implementation of this embodiment, a first common elevation is applied to the masked areas. A second common elevation, lower relative to the first common elevation, is then applied to the unmasked areas. The difference between the two common elevations is the expected average width of the resist layer. The program logic then interpolates the edges of the areas at the first common elevation, emulating the sidewalls which will be formed between the two elevations. Algorithms which emulate the behavior of the resist material are incorporated into the program logic in order that the resulting interpolated sidewalls are a reasonable approximation of the feature sidewalls which will be formed when the device is manufactured.

The simulation performed by the present invention thus goes further than simply creating sidewalls based on a standard slope. The system of the present invention analyzes the masked areas in light of known resist characteristics, and modifies the resulting emulated features, including sidewalls, according to anticipated resist behavior. As a result of the described procedure, defects caused by anomalies in the mask or poorly designed features are represented as they are expected to appear on devices manufactured using the mask being inspected, and mask deficiencies can be identified and potentially costly resist defects avoided.

According to one embodiment, the simulation program logic is written in the C programming language and compiled into machine-executable code. Those skilled in the art will recognize, however, that other programming languages may be used without exceeding the scope and spirit of the present invention. Comrnercially available simulation software does not currently provide the functionality required to perform a three-dimensional analysis of masks. One software product which employs three-dimensional simulation is Prolith™. This product is, however, designed for a different type of analysis and is too slow and overly detailed, making it unacceptable for a mask inspection application. Other software products can simulate resist images from mask data, but they are not intended to be used to simulate resist images from insetion data Faim™, from Vector Technology, and Proxima™ and Proteus™, from Precim, are examples of existing software used for image simulations.

As previously discussed, image data derived from original pattern data 150 is processed through image simulation circuitry, creating a second simulated image 185. The simulation process for each image incorporates logic which modifies the image data according to known characteristics of the resist used for forming a wafer. The two images 180 and 185 simulate the resist pattern; image 180 corresponding to original pattern data 150 and image 185 corresponding to mask image 160.2. These images 180 and 185 are then forwarded to and compared by defect detection circuitry 140 for defects.

Figure 2:
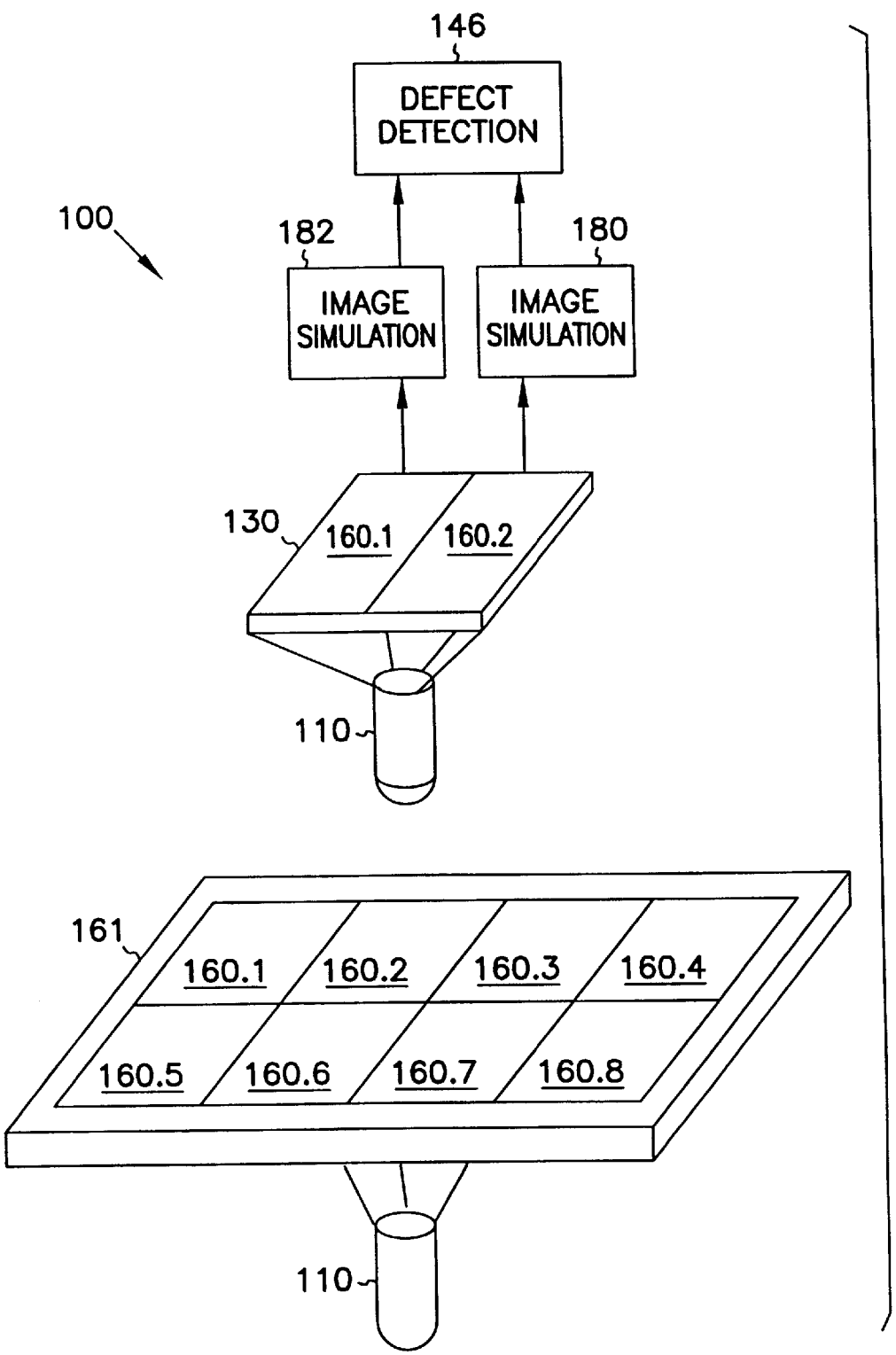
FIG. 2 illustrates a die-to-de inspection system according to an alternative embodiment of the present invention.

FIG. 2 illustrates a die-to-die inspection system according to an alternative embodiment of the present invention. A plurality of images are acquired through the same inspection machine 100 or another inspection machine connected to image simulation circuitry 180. In this embodiment, instead of comparing acquired image 160.2 to the image derived from pattern database 150, multiple acquired images are compared to each other. In this illustrative embodiment, acquired image 160.1 is compared to acquired image 160.2

The die-to-die mask inspection machine 100 thus comprises mask 161 having a plurality of identical patterns 160.1–160.8 wherein two or more wafer patterns are projected onto image sensor 130. In FIG. 2, first pattern 160.1 and second pattern 160.2 are projected onto image sensor 130 wherein image simulation circuitry acquires image data of the two patterns. The acquired image data corresponding to each pattern is modified to characteristics of resist materials used for forming a wafer using mask 161. After the image data is modified, image simulation 180 corresponding to first pattern 160.1 is formed and image simulation 182 corresponding to second pattern 160.2 is formed. Image simulations 180 and 182 are compared by defect detection 146 for defects.

Image simulation circuitry 180 is operationally independent from the other process modules 140, 150. This allows a flexible implementation of the present invention. In one embodiment, simulation 185 of original data 150 is performed off-line. According to one embodiment this step is performed on a machine separate from but connected to the inpection machine 100. In another embodiment it is performed on the inspection machine 100 prior to the actual inspection process.

Performing the simulation of the original data off-line increases efficiency by freeing up more resources for inspection processing. Generally the speed of an inspection system is directly related to the scanning speed of the mask. In one embodiment of the present invention, data processing is performed on the fly. As a result, simulating the resist image from the pattern acquired from the mask has limited impact on overall inspection time because it can be done in parallel to other inspection processing.

Inspection systems such as the KLA 351™ support parallel processing channels, enabling the addition of more computational power as necessary. The implementation of the system of the invention therefore provides extended pattern analysis without significantly increasing the overhead associated with mask inspection.

In one embodiment of the present invention, image simulation circuitry 180 is incorporated into inspection machine 100. Alternatively, image simulation circuitry 180 is incorporated in a system physically separate from the inspection machine. Data and control information may be communicated via network or any type of removable media Those skilled in the art will recognize that a variety of configurations may be employed without exceeding the scope and spirit of the present invention.

Figure 3:
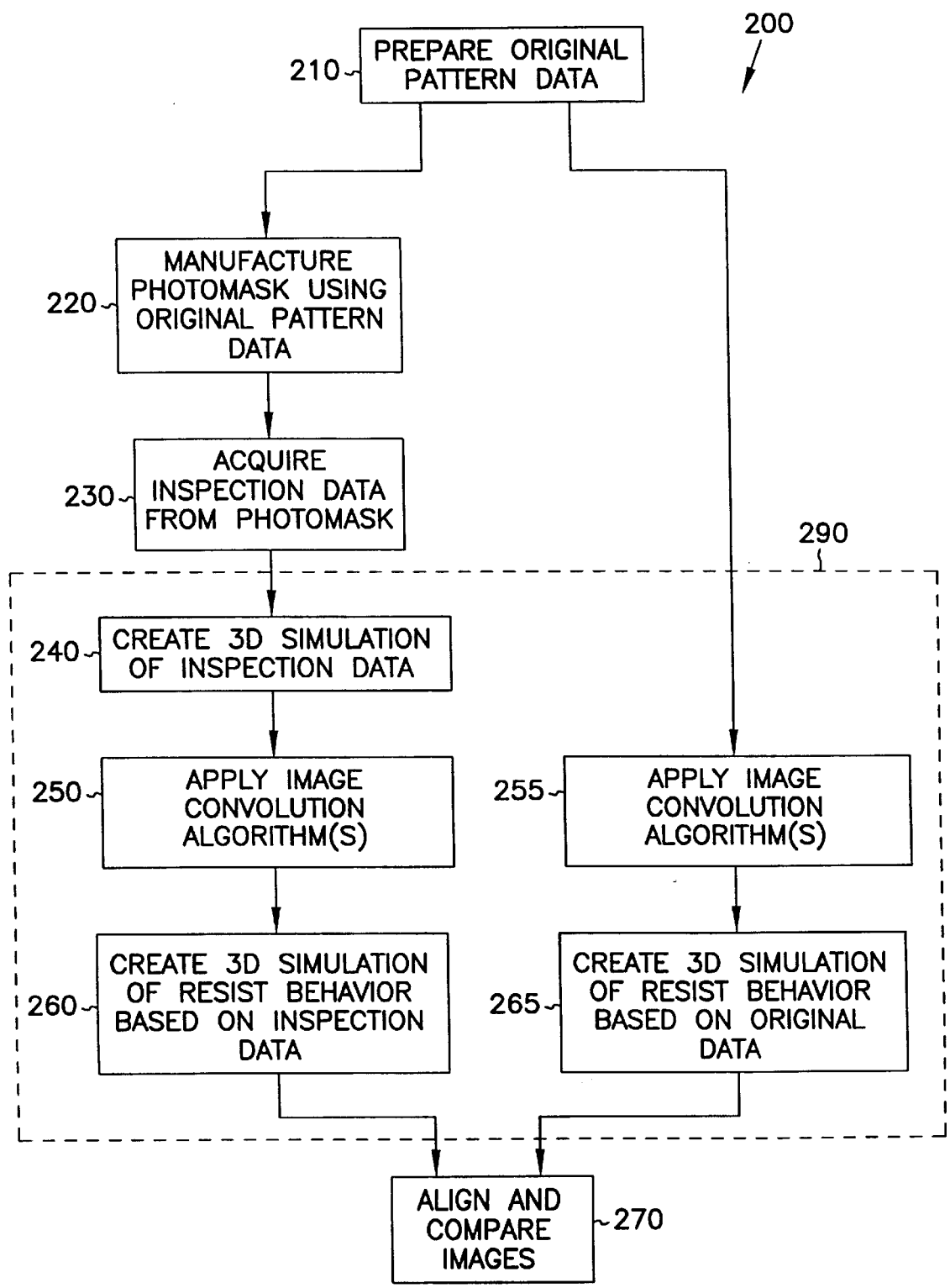
FIG. 3 is a flow diagram illustrating the logic followed by the die-to database inspection system.

FIG. 3 shows the logic followed by the image processor according to the die-to-database inspection system embodiment of the present invention. At the first process block 210, the original pattern data describing the features to be fabricated is prepared. This step comprises the well-known process of quantifing the features of the mask in two dimensional space so that a mask representing those features may be fabricated. The next step of the process 220 is to manufacture a mask using the original pattern data.

Once the mask is created, inspection data is acquired at process block 230. In one embodiment this step comprises taling an image from the mask and digitizing it using conventional mask inspection equipment. A simulation of the data is then created at process block 240. In one embodiment, the simulation is three dimensional. In an alternate embodiment the simulation is two dimensional. One reason the two-dimensional embodiment may be employed is to reduce the amount of data that is required to perform the analysis.

A modified data set is created to retain the resulting digitized raw simulation data. At the next process block 250 the raw simulation data set is manipulated according to algorithms emulating particular characteristics of the exposure tool and resist material. A refined simulation of the modified image data is then created at process block 260. The simulation steps employing the mask image data 240, 250, 260 are preferably performed in real time, as a large amount of data is collected and processed during the various steps.

In a separate process sequence, at process block 255 similar resist simulation algorithms are applied to the original pattern data set, creating a simulation of the modified original pattern data at process block 265. This step may be performed on the inspection system. Alternatively, it may be performed offline prior to mask inspection, thereby reducing processing overhead when mask inspection is performed.

At process block 270 the two process flows are brought together and the image simulations are aligned and compared. In one embodiment of the present invention the image simulation steps 260 and 265 are performed by commercially available software packages, and image simulation comparison is performed by conventional inspection devices.

Figure 4:
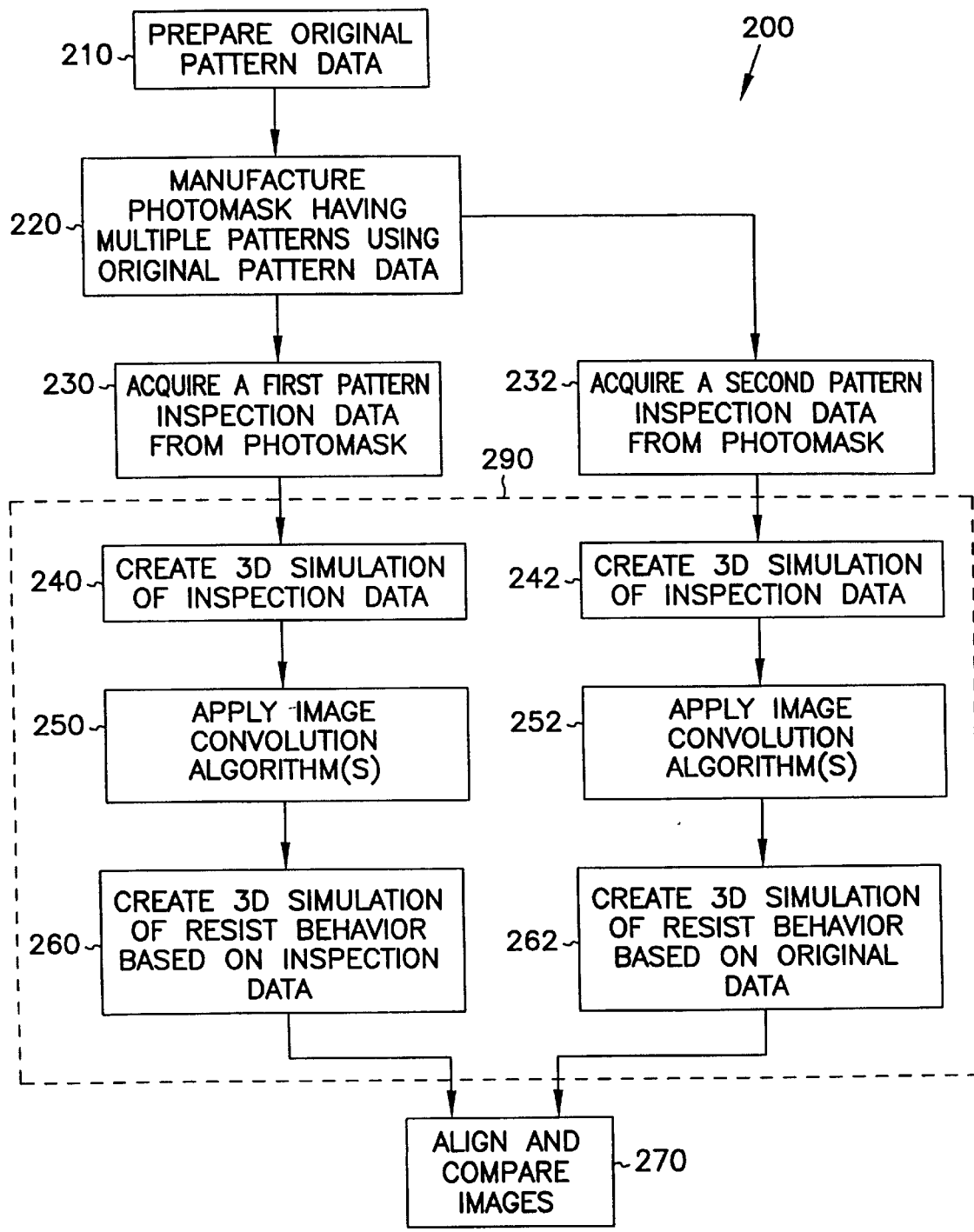
FIG. 4 is a flow diagram illustrating the logic followed by the die-to-die inspection system.

FIG. 4 shows the logic followed by the image processor according to the die-to-die inspection system embodiment of the present invention. At the first process block 210, the original pattern data describing the features to be fabricated is prepared. The next step of the process 220 is to manufacture a mask having a plurality of identical patterns formed by the original pattern data.

Once the mask is created, inspection data is acquired at process block 230 and 232, where process block 230 corresponds to a first pattern on the mask and process block 232 corresponds to a second pattern on the mask. In one embodiment this step comprises taking the images from the mask and digitizing them using conventional mask inspection equipment. Simulations of the data are then created at process blocks 240 and 242. In one embodiment, the simulation is three dimensional. In an alternate embodiment the simulation is two-dimensional.

A modified data set is created to retain the resulting digitized raw simulation data. At the next process blocks 250 and 252, the raw simulation data sets are manipulated according to algorithms emulating particular characteristics of the exposure tool and resist material. Refined simulations of the modified image data is then created at process block 260 and 262 for the first and second patterns. The simulation steps employing the mask image data 240 and 242, 250 and 252, 260 and 262 are preferably performed in real time, as a large amount of data is collected and processed during the various steps.

At process block 270 the two process flows are brought together and the image simulations are aligned and compared for defects. Incorporating multiple simulations of the mask images provides more accurate analysis of the mask features. The alignment process 270 includes logic to deal with any run-time bias between the images being aligned.

Figure 5:
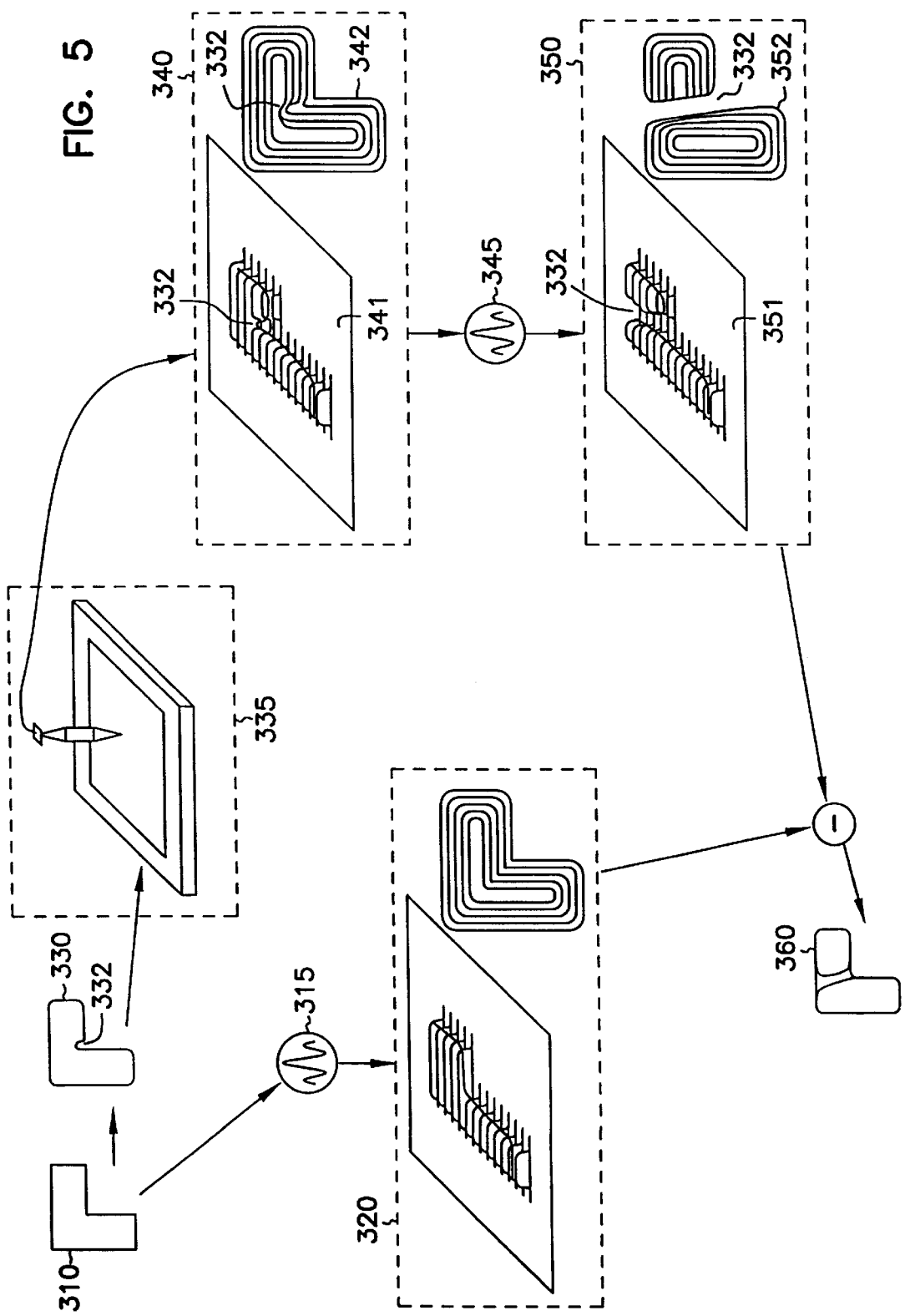
FIG. 5 is a pictorial representation of one embodiment of the method of the present invention.

FIG. 5 is a pictorial representation of one embodiment of the method of the present invention. First the original pattern is designed and described by a set of digital data 310. This set of original data is processed through simulation software 315. In the embodiment illustrated, during this process the original two-dimensional pattern is convoluted to create a three-dimensional simulation of resist behavior 320 (shown in both perspective and top view). The original data 310 is also used to manufacture a mask 330.

According to the example shown, a defect 332 is introduced during mask manufacture. Mask 330 is then inspected on image capture system 335, which digitizes the mask image. Program logic incorporated in image simulation circuitry 180 converts the digitized mask image to a three-dimensional data image 340 (show in both a perspective view 341 and top view 342). Note the subtle anomaly 332 caused by a mask defect in mask 330.

An erosion algorithm is included in the program logic for emulating the effect of mask defects on feature formation. One such algorithm is pixel erosion, which is a well-known image processing technique. Those skilled in the art will recognize that other erosion algorithms may be used without exceeding the scope of the present invention.

The program logic then creates a three-dimensional simulation of resist behavior 350 (show in both perspective view 351 and top view 352) from the digitized image 340. Note that by modifying the inspection image 340 according to resist characteristics 345 anomaly 332 is now a very visible defect 332. When the two resist simulations 320, 350 are compared 360 the defect 332 is easily detected. Those skilled in the art will recognize that this example is meant to be illustrative and not limiting in any way, and that other embodiments are possible.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A mask inspection system, comprising:
   a mask fabricated from a pattern;
   an inspection machine operable for acquiring image data from the mask and producing therefrom acquired mask image data;
   a processor operable for adding elevation data to the acquired mask image data and producing therefrom acquired mask elevation image data;
   a processor operable for creating a first simulated image using the acquired mask elevation image data according to the behavior of a resist material;
   the processor further operable for acquiring image data from the pattern and producing therefrom acquired pattern image data;
   the processor further operable for creating a second simulated image using the acquired pattern image data; and
   the processor further operable for comparing the first and second simulated images for defects in the mask.

2. The mask inspection system of claim 1, wherein the processor is further operable modifying the acquired pattern image data to characteristics of resist materials used for forming a wafer using the mask.

3. A method of inspecting a mask, comprising:
   acquiring mask image data by imaging the mask;
   adding elevation data to the acquired mask image data and producing therefrom acquired mask elevation image data;
   generating a first image simulation of the acquired mask elevation image data according to the behavior of a resist material;
   acquiring image pattern data from a pattern used for forming the mask;
   generating a second image simulation of the acquired image pattern data; and
   comparing the first and second image simulations for a defect in the mask.

4. The method of claim 3, wherein adding elevation data to the acquired mask image data includes:

applying a first common elevation to a mask area of the acquired mask image data;
applying a second common elevation to an unmask ed area of the acquired mask image data; and
interpolating an edge between the mask area and the unmasked area of the acquired mask image data at the first common elevation.

5. A method of inspecting a mask, comprising:
   acquiring mask image data by imaging the mask;
   generating a first image simulation of the acquired mask image data;
   acquiring pattern image data from a pattern used for forming the mask;
   adding elevation data to the acquired pattern image data and producing therefrom acquired pattern elevation data;
   generating a second image simulation of the acquired pattern elevation image data according to the behavior of a resist material;
   comparing the first and second image simulations for a defect in the mask.

6. The method of claim 5, wherein adding elevation data to the acquired pattern image data includes:
   applying a first common elevation to a mask area of the acquired pattern image data;
   applying a second common elevation to an unmasked area of the acquired pattern image data; and
   interpolating an edge between the mask area and the unmasked area of the acquired pattern image data at the first common elevation.

7. A method of inspecting a mask, comprising:
   acquiring image data of a first pattern by imaging the mask;
   adding elevation data to the acquired image data from the first pattern and producing therefrom acquired first pattern elevation image data;
   generating a first image simulation of the acquired first pattern elevation image data according to the behavior of a resist material;
   acquiring image data of a second pattern by imaging the mask;
   generating a second image simulation of the acquired image data from the second pattern; and
   comparing the first and second image simulations for a defect in the mask.

8. The method of claim 7, wherein adding elevation data to the acquired image data from the first pattern includes:
   applying a first common elevation to a mask area of the acquired image data from the first pattern;
   applying a second common elevation to an unmasked area of the acquired image data from the first pattern; and
   interpolating an edge between the mask area and the unmasked area of the acquired image data from the first pattern of the mask at the first common elevation.

9. A method of inspecting a mask, comprising:
   acquiring image data of a first pattern from the mask;
   generating a first image simulation of the acquired image data by imaging the first pattern;
   acquiring image data of a second by imaging from the mask;
   adding elevation data to the acquired image data by imaging the second pattern and producing therefrom acquired second pattern elevation data;

generating a second image simulation of the acquired second pattern elevation image data according to the behavior of a resist material; and comparing the first and second image simulations for a defect in the mask.

10. The method of claim 9, wherein adding elevation data to the acquired image data from the second pattern includes:

applying a first common elevation to a mask area of the acquired image data from the second pattern;

applying a second common elevation to an unmasked area of the acquired image data from the second pattern; and interpolating an edge between the mask area and the unmasked area of the acquired image data from the second pattern of the mask at the first common elevation.

11. A computer readable medium on a computer, the computer readable medium having computer executable instructions for performing a method comprising:

acquiring mask image data by imaging a mask;

adding elevation data to the acquired mask image data and producing therefrom acquired mask elevation image data;

generating a first image simulation of the acquired mask elevation image data according to the behavior of a resist material;

acquiring image pattern data from a pattern used for forming the mask;

generating a second image simulation of the acquired image pattern data; and comparing the first and second image simulations for a defect in the mask.

12. The computer readable medium of claim 11, wherein adding elevation data to the acquired mask image data includes:

applying a first common elevation to a mask area of the acquired mask image data;

applying a second common elevation to an unmasked area of the acquired mask image data; and interpolating an edge between the mask area and the unmasked area of the acquired mask image data at the first common elevation.

13. A computer readable medium on a computer, the computer readable medium having computer executable instructions for performing a method comprising:

acquiring mask image data by imaging a mask;

generating a first image simulation of the acquired mask image data;

acquiring pattern image data by imaging a pattern used for forming the mask;

adding elevation data to the acquired pattern image data and producing therefrom acquired pattern elevation data;

generating a second image simulation of the acquired pattern elevation image data according to the behavior of a resist material; and comparing the first and second image simulations for a defect in the mask.

14. The computer readable medium of claim 13, wherein adding elevation data to the acquired pattern image data includes:

applying a first common elevation to a mask area of the acquired pattern image data;

applying a second common elevation to an unmasked area of the acquired pattern image data; and interpolating an edge between the mask area and the unmasked area of the acquired pattern image data at the first common elevation.

15. A computer readable medium on a computer, the computer readable medium having computer executable instructions for performing a method comprising:

acquiring image data of a first pattern by imaging a mask;

adding elevation data to the acquired image data from the first pattern and producing therefrom acquired first pattern elevation image data;

generating a first image simulation of the acquired first pattern elevation image data according to the behavior of a resist material;

acquiring image data of a second pattern by imaging the mask;

generating a second image simulation of the acquired image data from the second pattern; and comparing the first and second image simulations for a defect in the mask.

16. The computer readable medium of claim 15, wherein adding elevation data to the acquired image data from the first pattern includes:

applying a first common elevation to a mask area of the acquired image data from the first pattern;

applying a second common elevation to an unmasked area of the acquired image data from the first pattern; and interpolating an edge between the mask area and the unmasked area of the acquired image data from the first pattern of the mask at the first common elevation.

17. A computer readable medium on a computer, the computer readable medium having computer executable instructions for performing a method comprising:

acquiring image data of a first pattern by imaging a mask;

generating a first image simulation of the acquired image data from the first pattern;

acquiring image data of a second pattern by imaging the mask;

adding elevation data to the acquired image data from the second pattern and producing therefrom acquired second pattern elevation data;

generating a second image simulation of the acquired second pattern elevation image data according to the behavior of a resist material; and comparing the first and second image simulations for a defect in the mask.

18. The computer readable medium of claim 17, wherein adding elevation data to the acquired image data from the second pattern includes:

applying a first common elevation to a mask area of the acquired image data from the second pattern;

applying a second common elevation to an unmasked area of the acquired image data from the second pattern; and interpolating an edge between the mask area and the unmasked area of the acquired image data from the second pattern of the mask at the first common elevation.

19. A mask inspection system, comprising:

a mask having a plurality of identical patterns, including a first pattern and a second pattern;

an inspection machine operable for acquiring image data of the first pattern and for acquiring image data of the second pattern and for producing therefrom first acquired image data and second acquired image data, respectively;

a processor operable for adding elevation data to the first acquired image data and producing therefrom first acquired elevation image data;

the processor further operable for creating a first simulated image using the first acquired elevation image data according to the behavior of a resist material;

the processor further operable for creating a second simulated image using the second acquired image data; and the processor further operable for comparing the first and second simulated images for defects in the mask.

20. The mask inspection system of claim 19, wherein the addition of elevation data to the first acquired image data by the processor includes:

the processor further operable for applying a first common elevation to a mask area of the first acquired image data;

the processor further operable for applying a second common elevation to an unmasked area of the first acquired image data; and the processor further operable for interpolating an edge between the mask area and the unmasked area of the first acquired image data at the first common elevation.

21. A mask inspection system, comprising:

a mask having a plurality of identical patterns, including a first pattern and a second pattern;

an inspection machine operable for acquiring image data of the first pattern and for acquiring image data of the second pattern and for producing therefrom first acquired image data and second acquired image data, respectively;

a processor operable for adding elevation data to the second acquired image data and producing therefrom second acquired elevation image data;

the processor further operable for creating a first simulated image using the first acquired mask image data;

the processor further operable for creating a second simulated image using the second acquired elevation image data according to the behavior of a resist material; and the processor fiuther operable for comparing the first and second simulated images for defects in the mask.

22. The mask inspection system of claim 21, wherein the addition of elevation data to the second acquired image data by the processor includes:

the processor further operable for applying a first common elevation to a mask area of the second acquired image data;

the processor further operable for applying a second common elevation to an unmasked area of the second acquired image data; and the processor further operable for interpolating an edge between the mask area and the unmasked area of the second acquired image data at the first common elevation.

23. A mask inspection system, comprising:

a mask fabricated from a pattern;

an inspection machine operable for acquiring image data from the mask and producing therefrom acquired mask image data;

a processor operable for adding elevation data to the acquired mask image data and producing therefrom acquired mask elevation image data;

the processor further operable for creating a first simulated image using the acquired mask elevation image data according to the behavior of a resist material;

the processor fuirther operable for acquiring image data from the pattern and producing therefrom acquired pattern image data;

the processor further operable for creating a second simulated image using the acquired pattern image data; and the processor further operable for comparing the first and second simulated images for defects in the mask.

24. The mask inspection system of claim 23, wherein the addition of elevation data to the acquired mask image data by the processor includes:

the processor further operable for applying a first common elevation to a mask area of the acquired mask image data;

the processor further operable for applying a second common elevation to an unmasked area of the acquired mask image data; and the processor further operable for interpolating an edge between the mask area and the unmasked area of the acquired mask image data at the first common elevation.

25. A mask inspection system, comprising:

a mask fabricated from a pattern;

an inspection machine operable for acquiring image data from the mask and producing therefrom acquired mask image data;

a processor operable for creating a first simulated image using the acquired mask image data;

the processor further operable for acquiring image data from the pattern and producing therefrom acquired pattern image data;

the processor further operable for adding elevation data to the acquired pattern image data and producing therefrom acquired pattern elevation image data;

the processor filrther operable for creating a second simulated image using the acquired pattern elevation image data according to the behavior of a resist material; and the processor further operable for comparing the first and second simulated images for defects in the mask.

26. The mask inspection system of claim 25, wherein the addition of elevation data to the acquired pattern image data by the processor includes:

the processor further operable for applying a first common elevation to a mask area of the acquired pattern image data;

the processor further operable for applying a second common elevation to an unmasked area of the acquired pattern image data; and the processor further operable for interpolating an edge between the mask area and the unmasked area of the acquired pattern image data at the first common elevation.

27. A computer program product, comprising:

a computer usable medium having a computer readable code means embodied therein for causing a detection of defects in a mask used in a photolithography system, the computer readable program code means in said computer program product comprising:

computer readable program code means for causing a computer to receive a set of digitized image data from the mask;

computer readable code means for adding elevation data to the digitized image data and producing therefrom digitized elevation image data;

computer readable program code means for causing a
computer to generate a first three-dimensional image
from the set of digitized elevation image data according
to the behavior of a resist material;

computer readable program code means for causing a
computer to receive a set of digitized image data from
a pattern used to defme the mask;

computer readable program code means for causing a
computer to generate a second three-dimensional
image from the set of digitized pattern data; and computer readable program code means for causing a
computer to compare the first and second three-
dimensional images for a defect in the mask.

28. The computer readable medium of claim 27, wherein computer readable code means for adding elevation data to the digitized image data includes:

computer readable code means for applying a first common elevation to a mask area of the digitized image data from the mask;

computer readable code means for applying a second common elevation to an unmasked area of the digitized image data from the mask; and computer readable code means for interpolating an edge between the mask area and the unmasked area of the digitized image data from the mask at the first common elevation.

29. A computer program product, comprising:

a computer usable medium having a computer readable code means embodied therein for causing a detection of defects in a mask used in a photolithography system, the computer readable program code means in said computer program product comprising:

computer readable program code means for causing a computer to receive a set of digitized image data from the mask;

computer readable program code means for causing a computer to generate a first three-demensional image from the set of digitized elevation image data;

computer readable program code means for causing a computer to receive a set of digitized image data from a pattern used to define the mask;

computer readable code means for adding elevation data to the digitized image data from the pattern used to define the mask and producing therefrom digitized elevation pattern data;

computer readable program code means for causing a computer to generate a second three-dimensional image from the set of digitized elevation pattern data according to the behavior of a resist material; and computer readable program code means for causing a computer to compare the first and second three-dimensional images for a defect in the mask.

30. The computer readable medium of claim 29, wherein computer readable code means for adding elevation data to the digitized image data from the pattern used to define the mask includes:

computer readable code means for applying a first common elevation to a mask area of the digitized image data from the pattern used to define the mask;

computer readable code means for applying a second common elevation to an unmasked area of the digitized image data from the pattern used to define the mask; and computer readable code means for interpolating an edge between the mask area and the unmasked area of the digitized image data from the pattern used to define the mask at the first common elevation.

31. A computer program product, comprising:

a computer usable medium having a computer readable code means embodied therein for causing a detection of defects in a mask having a plurality of identical patterns, including a first pattern and a second pattern, in a photolithography system, the computer readable program code means in said computer program product comprising:

computer readable program code means for causing a computer to receive a set of digitized image data from the first pattern;

computer readable code means for adding elevation data to the digitized image data from the first pattern and producing therefrom digitized elevation image data from the first pattern;

computer readable program code means for causing a computer to generate a first three-dimensional image from the set of digitized elevation image data from the first pattern according to the behavior of a resist material;

computer readable program code means for causing a computer to receive a set of digitized image data from the second pattern;

computer readable program code means for causing a computer to generate a second three-dimensional image from the set of digitized image data from the second pattern; and computer readable program code means for causing a computer to compare the first and second three-dimensional images for a defect in the mask.

32. The computer readable medium of claim 29, wherein computer readable code means for adding elevation data to the digitized image data from the first pattern includes:

computer readable code means for applying a first common elevation to a mask area of the digitized image data from the first pattern;

computer readable code means for applying a second common elevation to an unmasked area of the digitized image data from the first pattern; and computer readable code means for interpolating an edge between the mask area and the unmasked area of the digitized image data from the first pattern at the first common elevation.

* * * * *